(12) United States Patent
Mendel

(10) Patent No.: US 7,192,387 B2
(45) Date of Patent: Mar. 20, 2007

(54) FEEDBACK SYSTEM FOR MONITORING AND MEASURING PHYSICAL EXERCISE RELATED INFORMATION

(75) Inventor: Israel Mendel, Haifa (IL)

(73) Assignee: Dintex, Ltd., Haifa (IL)

( * ) Notice: Subject to any disclaimer, the term of this patent is extended or adjusted under 35 U.S.C. 154(b) by 516 days.

(21) Appl. No.: 10/415,592

(22) PCT Filed: Oct. 10, 2001

(86) PCT No.: PCT/IL01/00936

§ 371 (c)(1), (2), (4) Date: Apr. 30, 2003

(87) PCT Pub. No.: WO02/37732

PCT Pub. Date: May 10, 2002

(65) Prior Publication Data

US 2004/0014567 A1    Jan. 22, 2004

(51) Int. Cl.
 *A63B 21/00* (2006.01)
 *A63B 22/00* (2006.01)
(52) U.S. Cl. .................. 482/8; 482/1; 482/9; 482/900; 434/247
(58) Field of Classification Search ................ 482/1–9, 482/900–902; 434/247; 359/629, 630; 73/379.01
See application file for complete search history.

(56) References Cited

U.S. PATENT DOCUMENTS

| | | | |
|---|---|---|---|
| 4,387,437 A | 6/1983 | Lowrey et al. | |
| 4,563,003 A | 1/1986 | Bugallo et al. | |
| 4,746,113 A | 5/1988 | Kissel | |
| 4,962,469 A | 10/1990 | Ono et al. | |
| 5,655,997 A | 8/1997 | Greenberg et al. | |
| 5,689,099 A | 11/1997 | Domburg | |
| 5,724,265 A | 3/1998 | Hutchings | |
| 5,785,632 A | 7/1998 | Greenberg et al. | |
| 6,132,337 A | 10/2000 | Krupka et al. | |
| 6,159,130 A | 12/2000 | Torvinen | |
| 6,244,988 B1 | 6/2001 | Delman | |
| 6,669,600 B2 * | 12/2003 | Warner | 482/8 |
| 6,685,480 B2 * | 2/2004 | Nishimoto et al. | 434/247 |
| 6,765,726 B2 * | 7/2004 | French et al. | 359/630 |
| 6,808,473 B2 * | 10/2004 | Hisano et al. | 482/8 |

FOREIGN PATENT DOCUMENTS

| | | |
|---|---|---|
| DE | 42 13 442 | 10/1993 |
| FR | WO 96/29121 | 9/1996 |
| GB | WO 88 06909 | 9/1988 |

* cited by examiner

*Primary Examiner*—Glenn E. Richman
(74) *Attorney, Agent, or Firm*—Blank Rome LLP

(57) ABSTRACT

A system for advising an exerciser about his physical activities, associated either with displacement of the exerciser itself or of an object displaced by the exerciser, or an object displaced simultaneously with the exerciser. The system comprises a first unit for monitoring the activities. This unit is not in physical contact with the exerciser or the object, displaced by the exerciser. The first unit is capable to collect raw data defining the activities either in terms of distance or acceleration. The first unit transmits the collected raw data in a wireless fashion to a second unit, which receives the transmitted raw data, processes it and calculates various parameters, defining the said physical activities, and represents the calculated parameters in a form recognizable by the exerciser. The system enables tracking, recording and updating the relevant information, provides improved feedback and thus helps to the exercising individual to improve his performances.

16 Claims, 9 Drawing Sheets

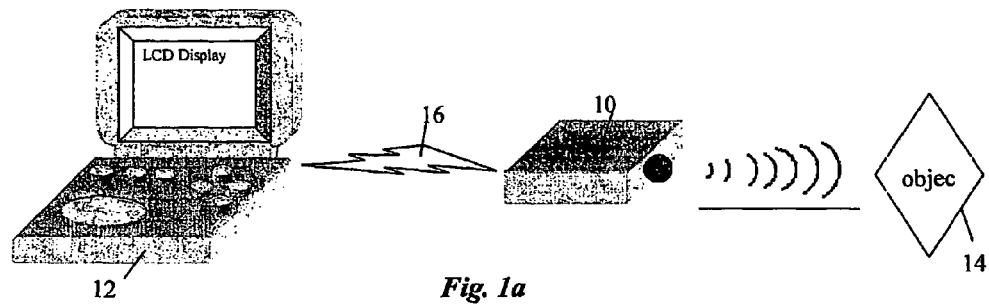
Fig. 1a
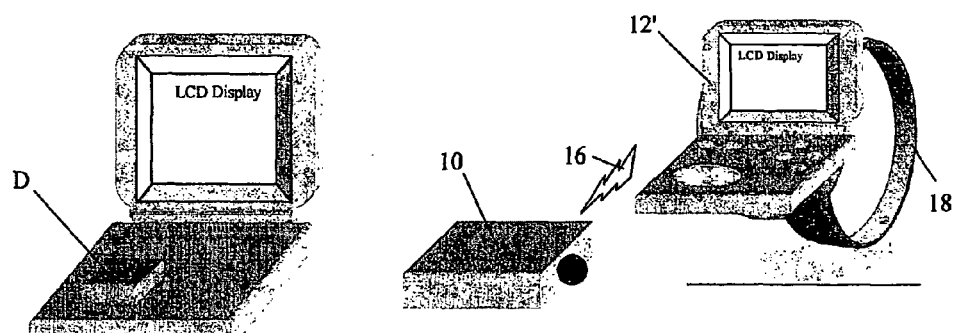
Fig. 1b
Fig. 1c
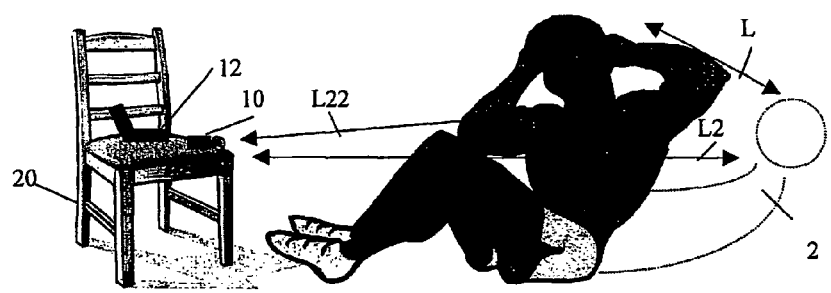
Fig. 2a

FEEDBACK SYSTEM FOR MONITORING AND MEASURING PHYSICAL EXERCISE RELATED INFORMATION

The present application is a national phase filing of PCT/IL01/00936(WO02/37732), filed Oct. 10, 2001, and claims priority to IL139387, filed Nov. 1, 2000.

FIELD OF THE INVENTION

The present invention relates to various physical exercise activities, more specifically it concerns monitoring and measuring of information relating to sport activities, during which an individual performs repetitious efforts, like sit-ups, push-ups, weight lifting, or efforts associated with distance displacement, e.g. running, skiing, horse riding, etc. The invention enables tracking, recording and updating the relevant information, provides improved feedback and thus helps to the exercising individual to improve his performances.

BACKGROUND OF THE INVENTION

Non-professional home sports, as well as some other professional sport branches are characterized by the fact that the individual usually trains alone, some times with no real opponent, which could stimulate and improve his performance, like time of exercise or effort. For example, in basic training exercises such as sit-ups, push-ups, or training with bar bells, the individual exercises for a certain period of time or till he gets tired. The result of the exercise in most cases is the number of repeated sit-ups or push-ups. The scores usually are not recorded anywhere and there is no proper follow up. Furthermore, there is no sufficient motivation in training alone. Some times, the counting is not accurate, because the exerciser concentrates on making the effort, rather than on the counting and the quality of the exercise.

The similar situation applies to physical activities associated with long distance moves, e.g. walking running, jogging, skiing etc.

In such cases, it would be desirable that the exercising individual is provided with a device that monitors his training and advises him about the performance for example by producing an audio/visual signal. This device could also keep a record of the current and previous performances and thus motivate and encourage the exerciser.

The above concept is not new and there is known in the art various fitness-monitoring devices, in which the above concept is implemented.

For example in U.S. Pat. No. 5,655,997 and 5,785,632 is disclosed an apparatus and system for providing feedback to a user of a weight stack machine. In this apparatus a means for sensing weight for determining the number of weights lifted is provided as well as encoder means for detection the motion of the weight during a lift. An electronic detector is operatively coupled to the weight sensor and the encoder for computing data describing the number of weight lifts.

In WO 96 96/29121 is disclosed a weight training apparatus for measuring a displacement in an exercise apparatus used for training or for rehabilitation. The apparatus comprises a peg for selecting part of a stack weights and this peg acts as a transmitter enabling a sensor system to sense the selected number of weights as well as the distance traveled by the weights, the time taken and their speed.

The apparatus comprises also a mechanism with scales attached to the machine along the travel route of the weights.

The disadvantage of both above-mentioned devices lies in the fact that they require sensing means, which should be directly attached to the weights for sensing the weights travel. This condition renders the above devices inconvenient in installation, limits their portability and excludes possibility for plug & play mode of operation.

In U.S. Pat. No. 4,387,437 is disclosed a runners watch, which is to be worn on the wrist of the wearer. The watch is provided with a sensor detecting the stride of the wearer when the wearer is running or jogging and with a circuitry, which calculates the distance traveled and the computed rate of travel. The disadvantage of this device is its limited applicability and insufficient accuracy, since a sensor employed in it is a mechanical pendulum, which can not sense travel not associated with strides, e.g. boating, skiing etc.

In U.S. Pat. No. 5,689,099 is disclosed speed/distance measuring assembly for runner, which measures angular displacement of the foot and the distance of the torso from a reference point. This approach is also not suitable for such displacements, like boating, horse riding or any other displacements, which are not associated with angular foot displacement.

In U.S. Pat. No. 4,962,469 is disclosed exercise measurement instrument, employing an acceleration sensor, connected to an amplifier. An output waveform signal of the acceleration sensor is supplied to the amplifier. The instrument is provided also with manually operable switching means for selecting one exercise mode out of plurality of modes available, amplifier gain-control means coupled to the switching means for varying the gain in accordance with the selected mode and exercise-measuring means for measuring exercise data on the basis of the waveform signal and announcing means for displaying the data measured. The disadvantage of this instrument is associated with the fact that the acceleration sensor resides not separately from the rest of the components, e.g. display means, data-entry means etc. but in the same enclosure. In such a configuration the accelerometer can not be always positioned accurately in the movement direction since each rotation or linear displacement of the instrument causes an error in the acceleration sensor reading, and consequently the velocity and position are calculated erroneously as well.

In U.S. Pat. No. 5,724,265 is described a system and method for measuring movement of objects, e.g. the distance traveled, speed and height jumped while running or walking. This system employs accelerometers and rotational sensors placed in the sole of one shoe along with an electronic circuit, which calculates the distance and height of each step. A radio frequency transmitter sends this data to a central receiving unit, which is formed as a wristwatch. The receiving unit calculates an output speed based upon step-distance and elapsed time and the total distance traveled. Unfortunately the approach implemented in the above patent is not suitable for monitoring of skiing, horse riding and boating.

Besides, location of the sensor unit in the shoe might be associated with limited reliability of operation and insufficient accuracy of measurement.

Thus despite there are known in the art plenty of methods and devices enabling an individual to monitor and measure his performances during physical activity, nevertheless there is still felt a strong need in a new and improved system and method, which is free of the above-mentioned disadvantages of the known in the art solutions.

SUMMARY OF THE INVENTION

The main object of the invention is to provide a new and improved system for monitoring and measuring physical activities of an individual enabling sufficiently reduce or overcome the above-mentioned drawbacks of the known in the art systems. In particular the main object of the invention is to provide a new and improved system, which is universal in the sense that it is suitable for monitoring various activities, including both repetitious movements, performed by an individual within the same location or activities associated with long distance displacements.

Still further object of the invention is to provide a new and versatile system, which suitable for monitoring long distance displacements irrespective whether it is running, skiing, walking, jogging, horse riding, boating, cycling etc.

Another object of the invention is to provide a new and reliable system, which enables accurate measuring of a physical activity.

Still further object of the invention is to provide inexpensive and compact system, which can be easily and fast installed in any premises, irrespective whether it is private house or professional sport hall or center.

The system of the present invention is a portable, pocket size, remote positioned electronic device that is capable to inform the exerciser about various parameters, associated with his activity, e.g. total number of exercises, elapsed time, number of executed exercises per minute, speed of each exercise, amount of gymnast's effort during the exercise, etc.

In accordance with the principle of operation it includes a first unit, which monitors and collects the raw data, associated with the physical activity (either distance or acceleration). The first unit transmits the raw data to a second unit, which processes it, calculates various parameters and announces them to the exerciser.

When it is required to monitor activities associated with repetitious exercises (push-ups, seat-up, weight lifting) the system uses the distance-based raw data and the first unit is placed in front of the exerciser (up to a few feet away). It can be placed on a chair, on the floor, or mounted on a weight stack machine itself or on the other sport equipment. There is no physical contact between the exerciser and the system. The second unit is placed in vicinity of the exerciser to enable him either to visually observe the parameters displayed or to hear them, or both. For example, each performance of a sit-up (which is considered a back and forth movement towards the first unit) can be accompanied by a beep sound (or a real counting voice) while incrementing a counter display. During exercising with a strength exerciser, the system can observe that the weights are pushed to the full predefined stroke, and therefore the exerciser is doing the exercise properly.

It can be readily appreciated, that the present system motivates the exerciser while he is training alone and helps him to follow up his training progress by controlling proper performance of the exercise (push-ups, set-ups, weight lifting workout with dumb-bells or bar bells, stepper machine workouts etc.) irrespective whether the exerciser performs it in a set, or till he stops. The system also enables recording the results of training.

When the system is used for monitoring physical activity associated with long distance displacements it uses acceleration-based raw data. In this embodiment, both the first and the second unit can be either worn by the exerciser or be separate from him, depending on the particular physical activity of the exerciser.

The above and other objects and advantages of the invention can be achieved by the system defined by the following combination of its essential features, referring to different embodiments thereof.

In accordance with the main embodiment it constitutes a system for advising an exerciser about his physical activities, said system comprises:
  a) a first unit for monitoring said activities, said first unit is capable to collect raw data defining the activities either in terms of distance or acceleration, said first unit is capable to transmit the collected raw data in a wireless fashion to
  b) a second unit, capable to receive the transmitted raw data, to process it and to calculate various parameters, defining the said physical activities, and to represent the calculated parameters in a form recognizable by the exerciser.

In accordance with one of the preferred embodiments said first unit comprises a housing with residing therein
  a) a means for generation of ultrasonic waves with modulated frequency, said means is capable to transmit pulses of modulated waves towards an object, which is being monitored during exercising and to sense pulses, associated with ultrasonic waves, reflected by the said object,
  b) an interface means, capable to activate said means for generation of ultrasonic waves, to measure the elapsed time between the transmitted and reflected pulse and to calculate value, corresponding either to distance or to acceleration
  c) a communication means capable to transmit the calculated value to the second unit.

In accordance with the further embodiment said second unit comprises a housing with residing therein
  a) an electronic circuit, provided with appropriate computing means for processing said raw data and calculating the said parameters,
  b) a memory storage means for storing the calculated parameters,
  c) an announcing means for advising the exerciser about the calculated parameters
  d) a link means for wireless communication with the first unit
  e) a power supply means for energizing the components of the second unit.

In yet another embodiment the housing of the first unit and of the second unit is provided with fastening means.

According to the further embodiment said announcing means comprises display for visual representation the calculated parameters.

In the additional embodiment said first unit is receivable within the housing of the second unit.

In yet further embodiment said means for generation of ultrasonic waves comprises an ultra-sonic sensor and said interface means comprises a micro-controller, capable to modulate frequency of transmitted ultra-sonic waves with pulses of about 1 millisecond.

According to another embodiment said computing means is selected from the group consisting of micro-controller and DSP chip, said display is a LCD module and said memory storage means is selected from the group consisting of EEPROM or FLASH memory chip.

And in still further embodiment said link means comprises a circuitry suitable for communication with the communication means of the first unit either in radio frequency or infrared frequency wavelength and said announcing means comprises loud speaker or a buzzer.

The present invention in its various embodiments has only been summarized briefly.

For better understanding of the present invention as well as of its advantages, reference will now be made to the following description of its embodiments with reference to the accompanying drawings.

BRIEF DESCRIPTION OF THE DRAWINGS

FIGS. 1a–c refer to various alternative configurations of the present system.

DETAILED DESCRIPTION OF SPECIFIC EMBODIMENTS

Figure 2B:
FIGS. 2a–3b refer to various applications of the present system for monitoring physical activities associated with repetitious displacements.

In FIG. 1 is shown general configuration of the system of the present invention. The system consists of two units, i.e. the first one, designated at 10 and a second unit 12, which is separate from the first unit. During performing physical activities the first unit is directed towards an object 14, associated with these activities and monitors these activities. The object is shown schematically and it should be understood, that in those situations, when the exerciser performs repetitious movements this object is the exerciser itself or any other object, associated with those movements e.g. weights of weight-lifting machine, dumbbells, etc. When the exerciser performs activities, associated with long distance displacements, e.g. boating, riding a bicycle, jogging etc. this object is a boat, a bicycle, the exerciser or any other moving object.

The first unit is intended for monitoring the moving object and collecting the raw data, associated with the movement in terms of distance or in terms of acceleration.

For the sake of brevity in the further description the first unit will be referred-to as monitoring unit and the second unit will be referred-to as processing unit. The first unit transmits the collected data through a wireless link 16 to the second unit, which processes the data and calculates particular parameters, defining the physical activity. The second unit also announces the exerciser about the calculated parameters.

In FIG. 1a the first and second unit is shown as compact, substantially rectangular box-like housing with residing inside electronic circuits and other necessary components, enabling its functioning. The housing can be provided with fastening means, e.g. clips, vacuum suckers, magnets, adhesive stripes etc. (not shown) for securing the unit on various surfaces or objects, associated with physical activity.

In FIG. 1b is shown, that housing of the processing unit is formed with a depression D dimensioned for receiving the monitoring unit. This might be useful, when the system is not functioning and should be stored in a compact configuration.

In FIG. 1c is shown another embodiment of the system, in which the processing unit is formed with as a clock 12', which can be worn on the exerciser's hand by virtue of a belt 18.

Referring now to FIGS. 2a–c and 3a–g it is shown how the system of the invention is used for monitoring physical activities, associated with repetitious movements or activities associated with long distance displacement.

As best seen in FIG. 2a the exerciser performs sit-ups, which are repetitious displacements between position 22 designated by solid line and position 24 designated by thin line. The monitoring unit 10 is placed on a chair 20 and it is directed on the exerciser to detect either the distance L22, when the exerciser is in position 22 or the distance L24, when the exerciser in position 24. The processing unit 12 can be placed on the same chair or be placed in any other location, from which it can be seen or heard by the exerciser. The monitoring unit detects every correct sit-rest movement between position 22 and 24 by sensing the distance L22 and L24. This data is transmitted to the processing unit and it produces an audio/visual response. The processing unit also keeps counting and recording the number of each correctly executed exercise.

In FIG. 2b the exerciser lies facing down on the floor and performs repetitious push-ups. The monitoring unit 10 is placed beneath the exerciser in front of its head or chest to detect distance L between the floor and the exerciser. Each correctly performed push up-down movement is accompanied by an audio/visual response, produced by the processing unit (not shown). It can be also recorded.

Figure 2C:
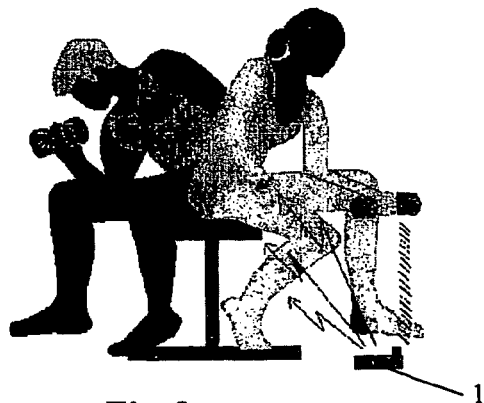
Figure 3A:
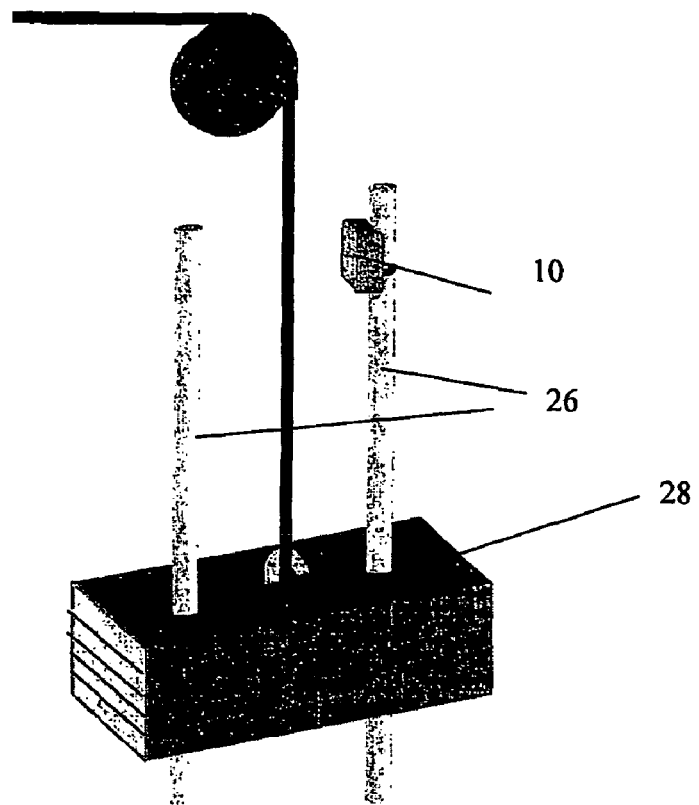
FIGS. 3c–g show application of the system for monitoring long distance displacement.
Figure 3B:
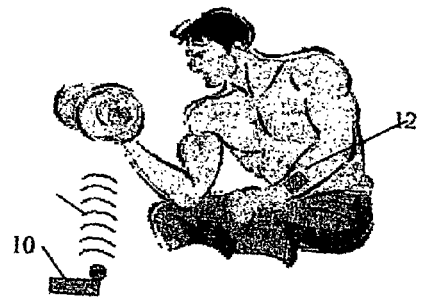

In FIGS. 2c, 3b are shown exercisers sitting on a chair and executing repetitious movements with a dumbbell. The monitoring unit 10 is placed on the floor beneath the hand of the exerciser holding the dumbbell. Each up-down movement of the dumbbell is associated with changing the distance between the dumbbell and the monitoring unit. This distance is detected, transmitted to the processing unit (not shown) and it produces an audio/visual response recognizable by the exerciser. The processing unit can be placed either in vicinity of the exerciser or worn by the exerciser on its hand.

In FIG. 3a is shown possibility for using the system when the exerciser uses facilities of a gymnastic hall, e.g. weight stack machine for repetitious lifting of weights. The monitoring unit 10 is attached to one of the leading bars 26 of the weights of the weight stack machine. The monitoring unit is located in such a manner, that it detects the travel of weights 28 and transmits the distance of travel to the processing unit (not shown). The processing unit calculates the travel rate and the number of up-down movements. It can also count the number of executed up-down movements and alert the exerciser when the pre-programmed 'time out' is over. The processing unit can also calculate the speed or change of speed of the travel and indicate the moment when the exerciser gets tired and therefore slows down the movement of weights.

Figure 3C:
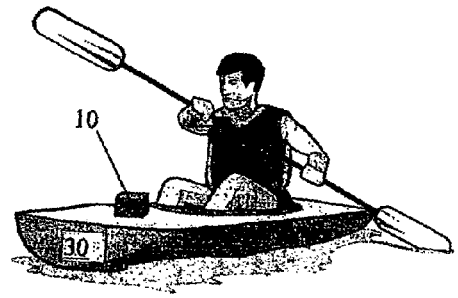
Figure 3D:
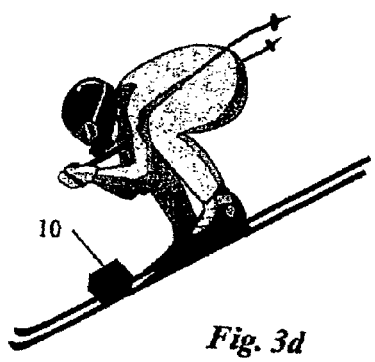
Figure 3E:
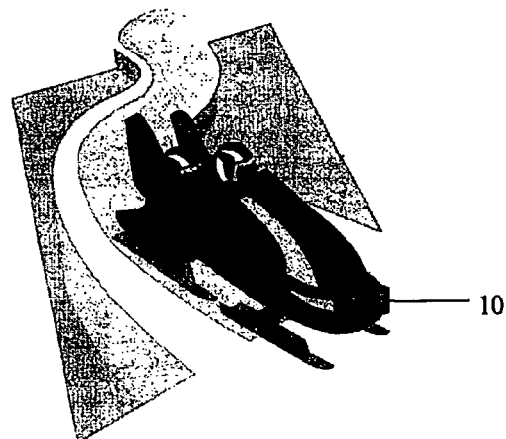
Figure 3F:
Figure 3G:
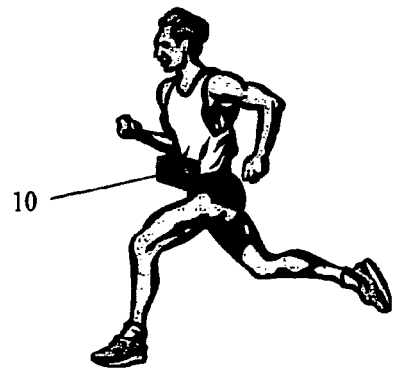

In FIG. 3c is schematically depicted how the system of the invention is implemented with physical activity associated with long distance displacements, e.g. rowing. The exerciser is rowing in a boat 30. The monitoring unit 10, which is located in the boat senses its acceleration and transmits this data to the processing unit, which calculates the value of the acceleration and additional parameters, like distance and announces the parameter to the exerciser. In FIGS. 3d–g are shown another examples of physical activities associated with long distance displacements, e.g. skiing, bobsledding, riding, jogging, etc.

Figure 4A:
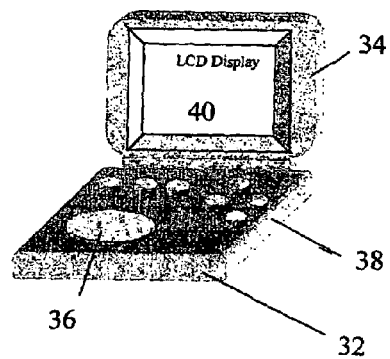
FIGS. 4a,b show various embodiments of the second unit.

Now with reference to FIGS. 4a,b,c and 5a,b it will be disclosed in details the construction of the above mentioned monitoring and processing unit.

In FIG. 4a a processing unit is shown, which housing is configured as an open book, consisting of a main portion 32 and foldable with respect thereto an auxiliary portion 34. Within the main portion are mounted all necessary electronic components (will be described later on) and on the upper part of the main portion are seen a loudspeaker 36 for audio announcing and knobs 38 of a keyboard interface.

Mounted on the auxiliary portion an LCD or LED display 40 for visual announcement is provided.

Figure 4B:
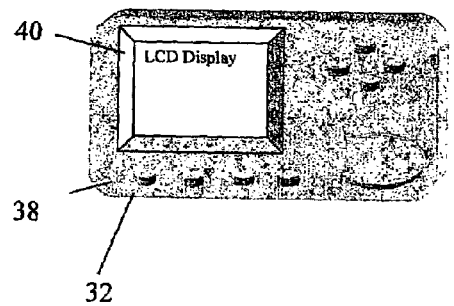
FIG. 4c shows the electronic components of the processing unit.

In accordance with the embodiment seen in FIG. 4b the processing unit is configured as a single piece, provided with the same above-mentioned components.

Figure 4C:
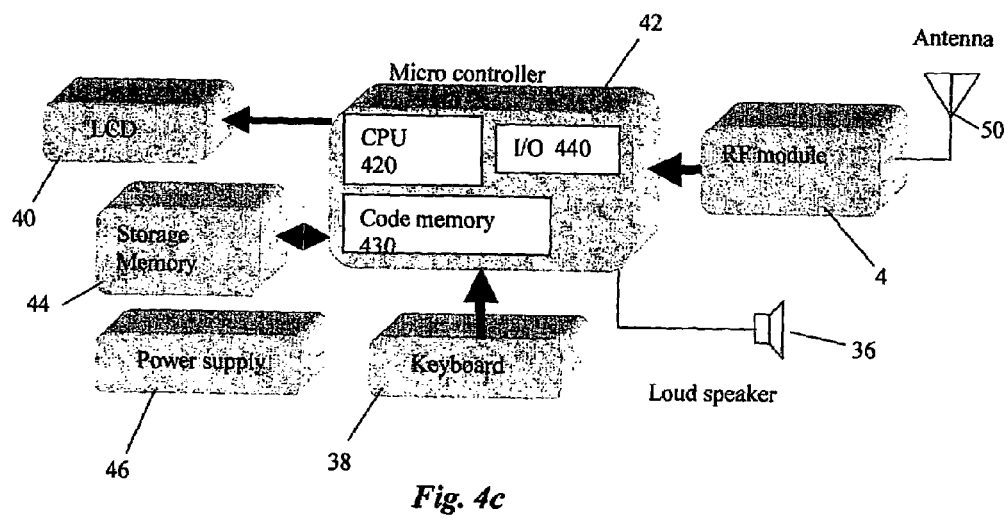

As best seen in FIG. 4c the electronic components of the processing unit comprise a computing means 42, a memory storage means 44, a power supply means 46, a communication means 48 with an antenna 50 for wireless link with the monitoring unit and a real time clock (RTC). The computing means such as micro controller or DSP chip consists of a CPU 420, a code memory 430 and an I/O circuit 440. The computing means has multiple functions: it manages the distance measurement and makes range calculations, it scans buttons of the keyboard to determine the operation mode, it activates circuitry of the display and loudspeaker and of the real time clock (RTC) to enable stopwatch functions. By virtue of the above functions it is possible to calculate scores referring to a specific day. to keep fitness statistics over a period of time, etc.

Examples of parameters, processed by the micro controller and displayed include:
Time and Date.
Instant exercise count/type.
Total number of repetitions required
Feed back for mode setting
Statistics during last week or month.

The audio signal, announced by the loudspeaker can be programmed to produce various sounds e.g. sounds corresponding to successfully executed exercise, faulted movement, beginning or end of the exercise, pressing of buttons of the keyboard, "Time Out" or "Low Battery" situation.

It might be also advantageous if the electronic circuit comprises speech synthesizer, to announce the above situations by a human-like voice.

The communication means, employed in the system is based on a short-range two-way RF (Radio frequency) data link. Each transmission begins with a header and sensor ID (identification), which corresponding to the addressed sensor.

The communication from the processing unit to the monitoring unit is compressed of a two bites transmission. Depending on the type of activities, performed by the exerciser (particular repetitious movement or long-distant displacement) the communication means activates the relevant sensor of the monitoring unit by transmitting an ON/OFF command via RF channel.

In response to transmission received from the monitoring unit the processor checks the first data byte (sensor ID) of each RF reception and determines accordingly the source of the transmission. Depending on this source the input data received by the processing unit is assigned to the relevant exercise, which is currently in progress.

It is not shown specifically, but should be understood, that the keyboard consists of a dedicated knobs, switches etc. to enable setting up the processing unit, selecting the exercise type, putting the voice accompaniment on or off, selecting the type of weights, setting up date, time and stopwatch.

The memory storage means 44 is capable to save the updated scores and exercise results. In practice the memory type can be either a low power RAM with a battery backup, or an EEPROM/FLASH MEMORY chip.

The power supply means comprises a "built in" pack of regular or rechargeable batteries. It can be readily appreciated that this provision renders the whole system portable and very convenient for the outdoor use.

Now with reference to FIGS. 5a,b the construction of the monitoring unit will be explained.

Figure 5A:
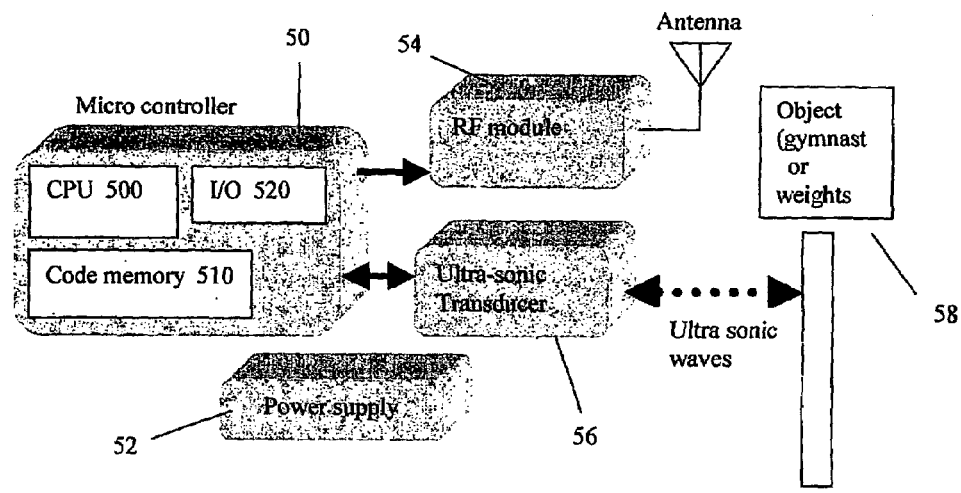
FIGS. 5a,b depict various embodiments of the first unit.

The embodiment shown in FIG. 5a refers to measurement of displacement associated with repetitious movements.

In accordance with this embodiment the monitoring unit is provided with a computing means 50, a power supply means 52, a communication means 54 and an ultra-sonic transducer 56. In practice the type of the transducer is MA40B7, manufactured by MURATA or any equivalent. The sensor should be capable to sense the distance up to an object 58, situated in front of the monitoring unit. As explained above this object is the exerciser itself, or any physical item displacing during the exercise, e.g. weights of the weight-stacking machine. It is not shown specifically but should be born in mind that the monitoring unit is provided also with an interface means to activate said sensor. The suitable computing means is a micro controller type 87lpc764 or any equivalent. The computing means should be capable to process the raw data, sampled from the sensor and convert it to distance. The computing means comprises a CPU 500, a code memory 510 and an I/O circuit 520.

The communication means comprises suitable circuits capable to transmit the calculated distance to the processing unit via antenna by radio frequency or IR (Infra red) waves. The principle of motion detection carried out by the monitoring unit will be referred-to further as "pulse reflection method". This method is based on transmitting ultrasonic wave to an object, receiving reflected ultrasonic wave and measuring time T, elapsed between transmitted pulse and received pulse of the ultrasonic wave.

The relationship between the distance up to the object L and the elapsed time T is expressed by the following formula:

$$L = C \cdot T/2$$

where C is the velocity of sound.

The micro-controller generates a 40 kHz frequency. This frequency is modulated with pulses of about 1 millisecond and then the modulated ultrasonic waves are transmitted to the air via transducer 56. The ultrasonic waves hit the object 58 and are reflected back. The embedded micro-controller 50 calculates the time elapsed from the moment the pulse has been transmitted till receiving its echo. This time is proportional to the distance to the object.

Figure 6:
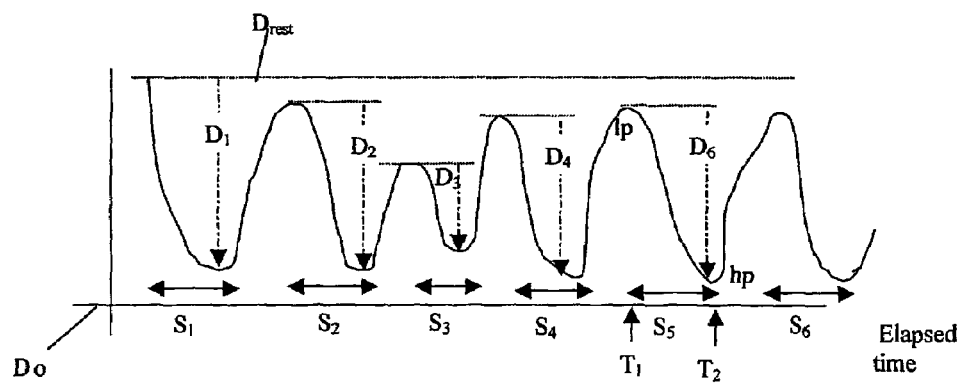
FIG. 6 schematically presents of monitoring of repetitious movements based on pulse reflection method

Now it will be explained how the above principle is used for monitoring physical activity associated with repetitious movements, e.g. lifting of weights as shown in FIG. 3a. As best seen in FIG. 6 the monitored object (weights of the lifting machine) are in the beginning of the exercise in a rest position, schematically designated as $D_{rest}$.

The monitoring unit is located at a distance $D_0$ from the weights. When the exercise begins the exerciser displaces the weights from the initial position towards the monitoring unit and then back to the initial position. Each up-down stroke S is schematically designated in FIG. 6 as $S_1, S_2, S_3, S_4, S_5, S_6$ etc. During each stroke the weights are displaced from instant initial position, designated as low peak LP to a position, designated as high peak HP. The elapsed time of the exercise is T. For each stroke a new distance ΔD is calculated from the preceding low peak LP to the subsequent high peak. For example this distance is $\Delta D_S=(D_1-D_2)$ for the first stroke, $\Delta D=(D_2-D_3)$ for the second stroke etc. The velocity of the movement is calculated by dividing the said distance to time ΔT, which is calculated for the first stroke as $\Delta T_S=(T_2-T_1)$, for the second stroke as $\Delta T_S=(T_3-T_2)$ etc., where $T_{i,j}$ is elapse referring to the subsequent and preceding stroke respectively.

It should be appreciated that this is not the only possibility for measuring of distance by calculating elapsed time between transmitted ultrasonic wave generated by ultrasonic transducer and reflected wave. Another possibility could be employing of an infrared transmitter and receiver.

Figure 5B:
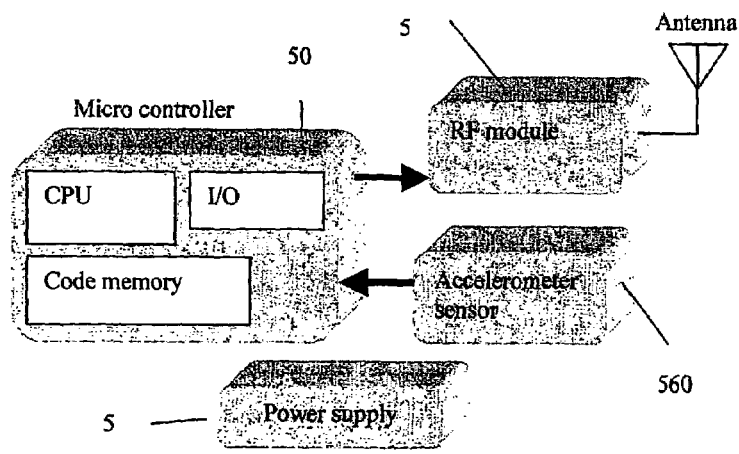

The embodiment of the monitoring unit shown in FIG. 5b refers to measurement of acceleration. As mentioned above this application is associated with measuring of physical activities referring to long distance displacement of the exerciser.

In this embodiment the unit is comprised of the components, common to the embodiment shown in FIG. 5a. These common components include computing means, e.g. micro controller 50, power supply 52, and communication unit 54. However, in contrast to the previous embodiment the monitoring unit shown in FIG. 5b is provided with a sensor 560, capable to measure acceleration. As suitable sensor one can use model ADXL202 manufactured by ANALOG DEVICES or any other equivalent.

The monitoring unit comprises also suitable interface means (not shown) to activate said sensor. The computing means such as micro controller type 87lpc764 or any equivalent is capable to process the raw acceleration data sampled from said sensor and convert it into speed and distance. In this embodiment, the preferable way to derive the speed is integration over time of the raw acceleration data. The displacement is derived by the second integration over time of the velocity data, obtained after the first integration. This method of monitoring of distance is especially advantageous, when it is required to monitor such activity like jogging, skiing etc, when the exerciser performs long distance displacement associated with steps. In the known in the art methods the distance usually is determined by counting of steps and then by multiply the number of steps taken by the average stride length.

It can be appreciated, that the resulting distance is affected by the change of the stride length and inaccuracy of the employed counting algorithms.

The communication means comprises radio frequency or IR (Infra red) circuits suitable to transmit said speed and distance to the processing means.

Figure 7A:
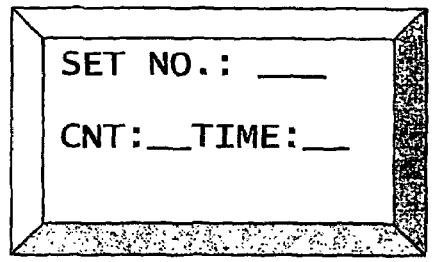
FIGS. 7a–c are examples of display of data, monitored by the system.
Figure 7B:
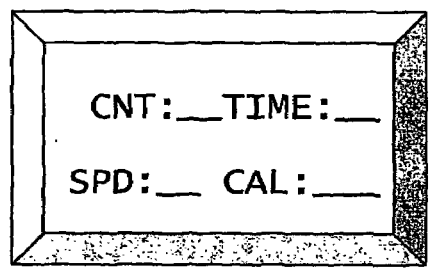
Figure 7C:
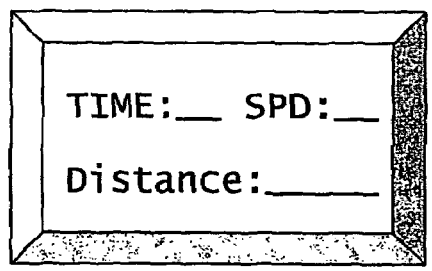

Now with reference to FIGS. 7a–c it is shown how results of the monitoring can be displayed by the system of the present invention. In FIG. 7a is shown an example of a display associated with monitoring of pushups or sit-ups exercises. The gymnast sees the total exercise time (TIME) that remains, count (CNT) of repetitions he has to do, and the set number (SET NO.).

In FIG. 7b is depicted a display of data, monitored during weight lifting exercise in a weight stack machines, or during training with dumbbells. The gymnast sees the total exercise time (TIME) that remains, count (CNT) of repetitions he has to do, speed (SPD) of the weights lifting, and total amount of calories (CAL) consumed.

In FIG. 7c is seen a display of data, monitored during an outdoor exercise, which is associated with long distance displacement such as jogging, horse riding, skiing, kayak rowing, etc. The gymnast sees the total exercise time (TIME) that remains, current speed (SPD) of the displacement, and total distance traveled so far (Distance).

It should be appreciated, that the present invention is not limited to the above-described embodiments and that the ordinary skilled in the art can make modifications without deviation from the scope of the invention, as it will be defined in the appended claims.

It should be also appreciated, that the features disclosed in the foregoing description, and/or the following claims, and/or in the accompanying drawings may, both separately and in any combination thereof, be material for realizing the present invention in diverse forms thereof.

I claim:

1. A system for advising an exerciser about his physical activities, associated an object displaced by the exerciser or an object displaced simultaneously with the exerciser, said system comprising a first unit monitoring the physical activities without being in physical contact with the exerciser or the said object, said first unit collecting raw data defining the physical activities either in terms of distance or acceleration, said first unit transmitting the collected raw data, said system further comprising a second unit positioned remote from said first unit, said second unit receiving the transmitted raw data from said first unit, processing the received raw data to calculate various parameters which define said physical activities, and representing the calculated parameters in a form recognizable by the exerciser.

2. The system as defined in claim 1, in which said first unit comprises:
   a) means for generation of preferably ultrasonic waves and for transmitting pulses of modulated waves towards the object, displaced by the exerciser or displaced simultaneously with the exerciser and to sense pulses, associated with the waves, reflected by said object,
   b) interface means, capable to activate said means for generation of ultrasonic waves, to measure the elapsed time between the transmitted and reflected pulse and to calculate value, corresponding either to distance to the monitored object or to acceleration thereof,
   c) communication means capable to transmit the calculated value to the second unit.

3. The system as defined in claim 1, in which said second unit comprises:
   a) electronic circuit, provided with appropriate computing means for processing said raw data and calculating the said parameters,
   b) memory storage means for storing the calculated parameters,
   c) announcing means for advising the exerciser about the calculated parameters,
   d) link means for wireless communication with the first unit,
   e) power supply means for energizing the components of the second unit.

4. The system as defined in claim 3, in which said announcing means comprises display for visual representation the calculated parameters.

5. The system as defined in claim 2, in which said means for generation of ultrasonic waves comprises an ultra-sonic transducer.

6. The system as defined in claim 2, in which said interface means comprises a micro-controller, capable to modulate frequency of transmitted ultra-sonic waves with pulses of about 1 millisecond.

7. The system as defined in claim 3, in which said computing means is selected from the group consisting of micro-controller or DSP chip.

8. The system as defined in claim 3, in which said memory storage means is selected from the group consisting of EEPROM or FLASH memory chip.

9. The system as defined in claim 3, in which said link means comprises a circuitry suitable for communication with the communication means of the first unit either in radio frequency or infrared frequency wavelength.

10. The system as defined in claim 3, in which said announcing means comprises loud speaker or a buzzer.

11. The system as defined in claim 1, in which said physical activities are associated with repetitious displacements of the object, displaced by the exerciser or with long distance displacements of the object displaced simultaneously with the exerciser.

12. The system of claim 1, wherein the physical activity comprises a strength training exercise having repetitious movement of the object, and further wherein the parameter calculated by said second unit comprises a number of repetitions of the object.

13. The system of claim 1, wherein said first unit is housed in a portable enclosure and includes an ultrasonic sensor and a magnet to removably attach said portable enclosure to the object.

14. The system of claim 13, wherein the object comprises a weight machine and said portable unit can be removably attached to leading bars of the weight machine, to a top of an upper weight plate, or to a metal housing of the weight machine.

15. The system of claim 1, wherein said second unit is housed in a portable enclosure and includes a magnet to removably attach said portable enclosure to the object.

16. The system of claim 15, wherein the object comprises a weight machine and said portable unit can be positioned on a metal housing of the weight machine in front of the exerciser or a trainer for viewing and provides results of the exercise.

* * * * *